United States Patent [19]
Giese et al.

[11] Patent Number: 5,512,486
[45] Date of Patent: Apr. 30, 1996

[54] SINGLE STEP SIGNAL GROUP-IMIDAZOLE LABELING OF ORGANIC PHOSPHATE GROUPS UNDER AQUEOUS CONDITIONS

[75] Inventors: Roger W. Giese, Quincy; Poguang Wang, Medford, both of Mass.

[73] Assignee: Northeastern University, Boston, Mass.

[21] Appl. No.: 60,569

[22] Filed: May 10, 1993

[51] Int. Cl.$^6$ .................................................. G01N 33/48
[52] U.S. Cl. .......................... 436/63; 436/94; 436/103; 436/104; 536/25.32; 548/335.1
[58] Field of Search ................... 536/25.32; 548/335.1; 435/6; 436/94, 63, 103, 104

[56] References Cited

U.S. PATENT DOCUMENTS

| | | | |
|---|---|---|---|
| 4,474,876 | 10/1984 | Osband et al. | 435/4 |
| 4,774,339 | 9/1988 | Haugland et al. | 548/405 |
| 4,830,961 | 5/1989 | Petty | 435/34 |
| 4,868,103 | 9/1989 | Stavrianopoulos et al. | 435/5 |
| 5,179,210 | 1/1993 | Ebel | 548/335.1 |

OTHER PUBLICATIONS

Ivanovskaya et al., "Modification of Oligo(poly)nucleotide Phosphomonoester Groups in Aqueous Solutions," *Nucleosides & Nucleotides* 6(5):913–934 (1987).
Larry J. Kricka, ed., "Nonisotopic DNA Probe Techniques," Academic Press, Inc.
Morrison et al., "Solution–Phase Detection of Polynucleotides Using Interacting Fluorescent Labels and Competitive Hybridization," *Anal. Biochem.* 183:231–244 (1989).
Sundberg et al., *J. Am. Chem. Soc.* 96(2); 381–392 (1974).
1991 Amersham Catalog, p. 244.
Chu et al., *Nucleic Acids Res.* 11(18), 6513–6529 (1983).
Al–Deen et al., *J. Chromatography* 512, 409–414 (1990).

*Primary Examiner*—W. Gary Jones
*Assistant Examiner*—Kenneth R. Horlick
*Attorney, Agent, or Firm*—Weingarten, Schurgin, Gagnebin & Hayes

[57] ABSTRACT

Compounds and methods for single step, covalent labeling of the phosphate group of an organic substance under aqueous conditions are described. The labeling compound includes any kind of detectable signal group covalently bound to an imidazole moiety, which can be imidazole or a substituted imidazole. A preferred labeling compound has the formula

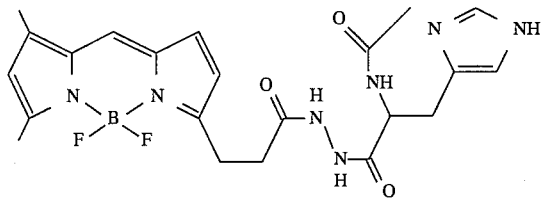

31 Claims, 3 Drawing Sheets

BO-IMI

BO-IMI

SINGLE STEP SIGNAL GROUP-IMIDAZOLE LABELING OF ORGANIC PHOSPHATE GROUPS UNDER AQUEOUS CONDITIONS

GOVERNMENT RIGHTS

Part of the work leading to this invention was made with United States Government funds through funding provided by the Department of Energy Grant DE-FG02-905R60964. Therefore, the U.S. Government has certain rights in this invention.

FIELD OF THE INVENTION

The invention is directed to single step, specific labeling of an organic phosphate compound under aqueous conditions.

BACKGROUND OF THE INVENTION

The phosphate group serves important functional purposes in biochemistry. It contributes to the structure and function of all major classes of organic biomolecules comprising proteins, lipids, carbohydrates and nucleic acids, along with precursors, combinations and metabolites of these substances. As biomolecules function under aqueous conditions, it is important to have chemical and physical tools and techniques for the detection and manipulation of organic phosphate compounds in their naturally occurring state, i.e., under aqueous conditions.

A gap that has existed in the study of phosphate compounds under aqueous conditions is the ability to specifically and usefully label the phosphate group of such compounds in a single step. Single step labeling means that other functional groups which may be present on the same or other compounds in the sample are not labeled, and that one does not form multiple derivatives of the targeted phosphate group which would make the labeling confusing and therefore not useful.

A great variety of labeling reagents bearing a detectable signal group and a reactive functional group are employed in analytical chemistry, including biochemistry, as has been reviewed (L. J. Kricka, *Nonisotopic DNA Probe Techniques,* Academic Press, San Diego, 1992). Most used for signal groups are radioisotopes (e.g., $^{32}P$, $^{33}P$, $^{35}S$, $^{125}I$, $^{3}H$, $^{14}C$), fluorophores (e.g., fluoresceins, rhodamine, tetramethylrhodamine, Texas Red, pyrene, coumarins, dansyl, BODIPY®s), lumiphores (e.g., luciferin, luminol, isoluminol, lanthanide chelates, acridinium esters), enzymes (e.g., horseradish peroxidase, alkaline phosphatase), haptens (e.g., digoxigenin, biotin, fluorene, dinitrophenyl), coenzymes (e.g., biotin), proteins (e.g., avidin, phycobiliproteins), nucleic acids, plastic particles (e.g., latex), liposomes (e.g., dye or enzyme-filled liposomes), metals (e.g., ferrocene), electrochemiphores (e.g., catechols, sugars), electrophores (e.g., pentafluorobenzyloxyphenyl ketones) and chromophores (e.g., Dabsyl, Malachite Green). The following reactive functional groups, or analogs or activated forms of these groups, have been employed on labeling reagents to form a stable bond to the target functional group on the substance of interest: succinimidyl esters, anhydrides, thiols, maleimides, acyl azides, acyl halides, isocyanates, sulfonyl chlorides, sulfonyl fluorides, hydrazines, amines, alkyl halides, haloacetyls, alcohols, aldehydes, glyoxals, hydrazides, and carboxylic acids (e.g., carbodiimide-activated). But none of these functional groups has been used, or has any ability to be used, to achieve specific labeling of a phosphate compound in a single step under aqueous conditions.

Polynucleotides containing a free phosphate group have been labeled on the phosphate moiety under aqueous conditions by reacting them with ethylenediamine in the presence of a water-soluble carbodiimide, followed by reaction of the residual amino group with an amino-reactive fluorophore (L. E. Morrison et al., Anal. Biochem. 183:231–244, 1989). However, not only does this procedure involve two reaction steps, but each of the reaction steps is nonspecific. Thus, if any contaminating carboxylic acids are present in the first reaction, they will also undergo coupling to the ethylenediamine. Further, if any contaminating amines are present in the second reaction, they will undergo labeling with the amine-reactive fluorophore.

Fluorescein-histamine has been prepared to stain (noncovalently) histamine or histamine blocker sites on mammalian cells (H. R. Petty, U.S. Pat. No. 4,830,961). A polymeric form of this type of reagent also has been introduced (M. E. Osband et al., U.S. Pat. No. 4,474,876). However, the reagents have not been used, or suggested for use, for covalent labeling of phosphate substances, or any kind of covalent labeling.

Mononucleotides have been labeled under aqueous conditions in a single step using a water-soluble carbodiimide with 2-(N-dansyl)-aminoethanol (M. G. Ivanovskaya et al., Nucleosides and Nucleotides 6:913–939, 1987). However, this is not a specific reaction for phosphate compounds, since carboxylic acids will also be labeled under these reaction conditions.

R. Haugland and H. C. Kang (U.S. Pat. No. 4,744,339) have disclosed that a dipyrromethaneboron difluoride dye can be substituted with a chemically reactive group capable of forming a chemical bond with a ligand.

SUMMARY OF THE INVENTION

The invention is directed to compounds and methods for single step, covalent labeling of the phosphate group of an organic substance under aqueous conditions. The labeling compound includes any kind of a detectable signal group covalently bound to an imidazole moiety, which can be imidazole or a substituted imidazole.

In one aspect, the invention features a signal group-imidazole labeling compound having the structure S—L—I wherein a signal group S is connected to one of the carbon atoms on an imidazole moiety I by a linking group L and wherein further the atoms of L that form a continuous chain between S and I, the atoms of L denominated the L backbone, number no more than 12; the L backbone includes at least one saturated atom when S is a boron-containing fluorescent moiety; S and L are each devoid of sulfhydryl, primary amino, arlyhydroxy and carboxyl groups; and S is not biotin. Preferably, the labeling compound includes one or more of the following features. The linking group can be connected to one of the two adjacent carbon atoms on the imidazole moiety or to the carbon atom between the two nitrogen atoms of imidazole. One of the two carbon atoms of the imidazole moiety to which the linking group is not attached can be substituted with a $C_1$–$C_6$ alkyl substituent, which in turn is substituted with 0–2 of the following substituents: hydroxy, ether, cyano, amide, ester, vinyl, aryl, sulfate, sulfonate, halogen, or sulfonaminde. The linking group can possess a branching substituent on the atom (which may be carbon or "C") attaching the linker to imidazole, or the branching substituent can be attached to the penultimate atom attaching L to I. The number of atoms in the L backbone is preferably 2–8, and the number of amino acid residues included in L can be one but preferably is zero. The signal group S can be derived from any reagent bearing a detectable signal group and a reactive functional group and is preferably one of the most used groups listed above. Most preferably, the labeling compound has the formula

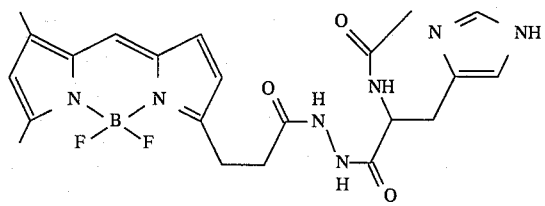

The invention also features a signal-imidazole labeling compound wherein a signal group is connected to the carbon atom between the two nitrogen atoms of an imidazole moiety. Preferably, at least one saturated carbon atom connects the signal group and the imidazole moiety.

In another aspect, the invention features a method for labeling an organic phosphate substance in aqueous solution that includes the steps of providing a signal group-imidazole labeling compound and covalently linking the labeling compound via the imidazole moiety, in the presence of an aqueous carbodiimide reagent, to a free phosphate moiety on an organic substance. The invention also features a molecular conjugate that includes a signal group-imidazole labeling compound covalently bound via the imidazole moiety to a free phosphate moiety on an organic substance.

BRIEF DESCRIPTION OF THE DRAWINGS

Other features and advantages of the invention will be apparent from the following description of the preferred embodiments thereof and from the claims, taken in conjunction with the accompanying drawings in which:

DESCRIPTION OF THE PREFERRED EMBODIMENTS

The method of the invention has solved the problem of specifically and usefully labeling a phosphate compound in a single step under aqueous conditions. If a carbodiimide-compatible label-linker group is established on one of the carbon atoms of imidazole (to form a label-imidazole reagent) and if the label-imidazole reagent is attached to a phosphate compound with aid of a water-soluble carbodiimide while later keeping the resulting label-linker-imidazole phosphate conjugate at an alkaline pH, single step, specific, useful phosphate labeling can be achieved. The key to the specificity of the invention is the hydrolytic instability of any label-linker-imidazole carboxylic acid conjugates that form, leaving the label-linker-imidazole moiety stably attached only to the phosphate compound at the conclusion of the process.

Figure 1:
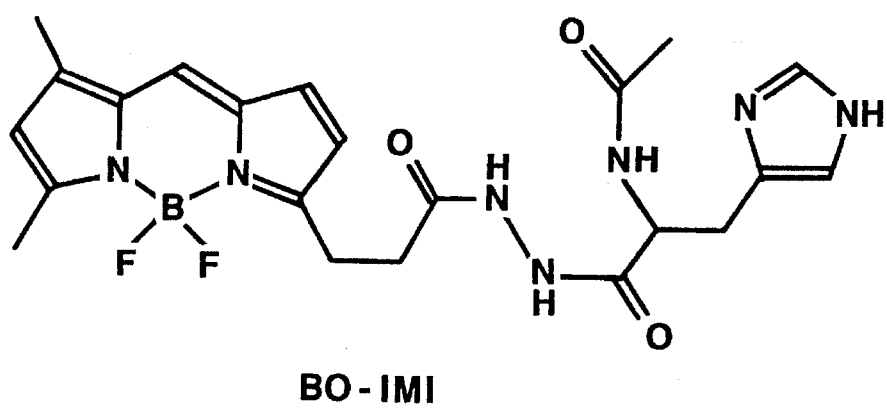
FIG. 1 shows a signal group-imidazole labeling compound of the invention.

Referring to FIG. 1, the invention can be illustrated by the preparation of the novel reagent shown as the compound "BO-IMI." To form this compound a carbodiimide-compatible fluorescent group consisting of a BODIPY® dye (Molecular Probes, Eugene, Oreg.) is attached via an eight atom carbodiimide-compatible linker group to one of the carbon atoms on imidazole. Importantly, neither the linker nor the signal moiety possesses a sulfhydryl, primary amino, arylhydroxy or carboxyl moiety, thus rendering the label and linker groups unreactive, and thereby compatible, with the water-soluble carbodiimide reagent used to attach the imidazole moiety to a phosphate compound.

It is especially attractive to employ a 2-(label-linker)imidazole reagent in which the linker is attached to the carbon atom (C2) between the two nitrogen atoms of imidazole. This is because the same product will result when either of the nitrogen atoms on the imidazole moiety of the 2-(label-linker)-imidazole reagent is attached to the phosphate moiety of the target substance to be specifically labeled.

To form the specific BO-IMI reagent tested, BODIPY®-FL $C_3$ hydrazide was coupled to the carboxyl group of N-acetyl-histidine. Both 5'- and 3'-deoxynucleoside monophophates, and some other phosphate compounds, were labeled with BO-IMI (via a phosphoroimidazolide linkage) in the presence of a water-soluble carbodiimide. Neither glycine nor albumin interfered with the labeling reaction. Cation exchange chromatography was used to purify the BO-IMI labeled compounds prior to their determination by capillary electrophoresis with laser fluorescence detection (argon ion laser, 488 nm). Storage of a model product, BO-IMI-dAMP, for one week at pH 8.7 at room temperature gave only 2% hydrolysis to reform BO-IMI, whereas the half-life for this hydrolysis at pH 5 was 4.7 hours.

Figure 2:
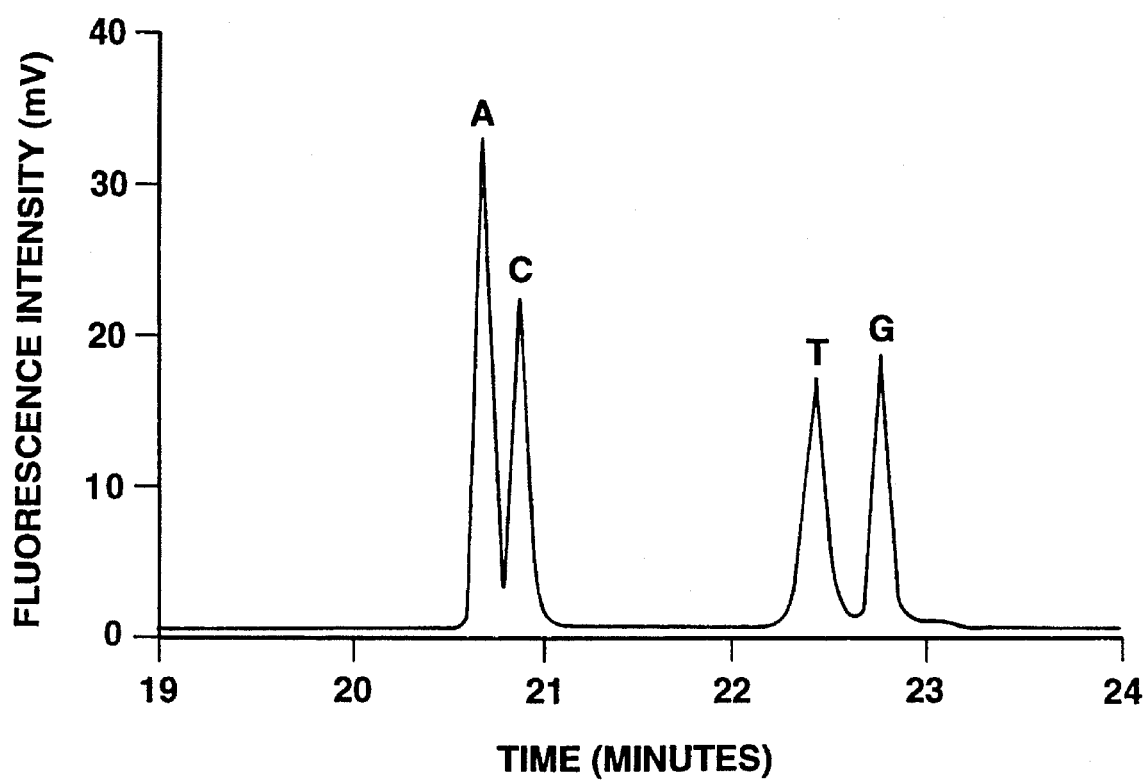
FIG. 2 shows capillary electrophoresis separation of a mixture of nucleotide monophosphates labeled with a labeling compound of the invention.

For example, reaction of a mixture of 5'-dAMP, 5'-dCMP, 5'-TMP and 5'-dGMP with BO-IMI in the presence of a carbodiimide (EDC) under aqueous conditions, followed by cation exchange chromatography (to remove both residual BO-IMI and EDC), and then injection into a capillary electrophoresis column with laser fluorescence detection (CE-LF), gave the electropherogram shown in FIG. 2. 5'-dAMP was labeled to the same extent with BO-IMI, with no evidence of side products by CE-LF, in the presence or absence of glycine (10-fold molar excess over 5'-dAMP) or in 1% albumin. This result is consistent with the hydrolytic instability of carbonylimidazoles (Anjaneyulu et al., Int. J. Peptide Protein Res. 30.:117–124, 1987), accounting for the specificity of BO-IMI for labeling a phosphate as opposed to carboxyl group.

BO-IMI-5'dAMP is relatively stable at alkaline pH but hydrolyses to reform BO-IMI under acidic conditions (e.g., $t_{1/2}$=2.7, 2.8, 4.7 and 19.7 hours at pH 2, 4, 5 and 6, respectively; no hydrolysis after 5 hours at pH 7–10.4; 2% hydrolysis after 1 week at pH 8.7; solutions stored at room temperature in the dark). Further, this conjugate is stable in 0.1M glycinamide, carbohydrazide, ethylenediamine, and mercaptoethylamine, and in 1% albumin, but reforms 24% BO-IMI in 0.1M imidazole; all after 2 hours at room temperature, pH 8.7.

Synthesis of BO-IMI

BODIPY® FL $C_3$ hydrazide (4,4-difluoro-5,7-dimethyl-4-bora3a,4a-diaza-s-indacene-3-propionyl hydrazide, 5 mg, from Molecular Probes, Eugene, Oreg.) in 0.75 ml of dimethylsulfoxide, 30 mg of N-acetyl-L-histidine, and 50 mg of 1-ethyl-3-(3-dimethylaminopropyl)-carobodiimide (EDC) in 2.1 ml of buffer A (0.5 ml of 0.2M MES, 0.06 ml of 0.1M NaOH, and 9.5 ml of water (pH 5.0)) were stirred for 1.5 hours at room temperature in the dark. The reaction mixture was applied to a column containing 500 mg of propyl sulfonic acid silica (J. T. Baker Inc., Phillipsburg, N.J.) that had been washed with 15 ml of buffer C (add 0.1M NaOH to 0.1M HEPES (pH 7.2)) until the eluent was pH 7.2. After the column was washed with 30 ml of buffer D (add 0.1M NaOH to 0.01M HEPES (ph 7.2)), the product was eluted with 7 ml of the supernate obtained by combining 9 ml of brine and 3 ml of methanol and extracted into 5×6 ml of ethyl acetate/acetonitrile, 1:1, v/v. The latter solution (BO-IMI Stock) of pure product (a single peak both by CE in buffer B (2.0 ml of 0.2M MES, 0.28 ml of 0.5M TRIS (pH 6.0)), which demonstrated the absence of BODIPY® FL $C_3$ hydrazide, and by HPLC, which also showed the absence of N-acetyl-L-histidine) was stored at −20° C. in the dark. Yield: (based on diluting 1:20 into methanol and using $\alpha$=71,000 at 503 nm; Haugland, R. P. "Handbook of Fluorescent Probes and Research Chemicals," Molecular Probes, Eugene, Oreg., 1992, p. 46) was 95%. HPLC conditions: Microsorb 86 -200-C5, C18-Si column, 5μ, 4.6 mm id×25 cm 1, Rainin, Woburn, Mass.; 0.05M phosphate, pH 7.1:acetonitrile, 70/30, 1 ml/min; N-acetyl-L-histidine (1.9 min), BO-IMI (9.5 min), BODIPY® FL $C_3$ hydrazide (15.1 min). FAB-MS: m/z 486 $(M+H)^+$.

Other Examples

Synthesis of 2-(2'-carboxyethyl)imidazole (2).

2-Iodopropionic acid (Aldrich Chemical Co.) is converted to t-butyl-3-iodopropionate by a standard reaction (T. W. Green and P. G. M. Wuts, *Protective Groups in Organic Synthesis*, John Wiley, N.Y., pp. 245–246). The latter compound is converted to 2-(2'-carboxyethyl)imidazole in the same way that 2-butylimidazole is prepared from imidazole (A. R. Katritzky et al., J. Org. Chem. 53:5685–5689, 1985), including conditions to remove the t-butyl group (Greene and Wuts, Ibid., p. 246).

Synthesis of 2-(3'-carboxypropyl)imidazole (3).

This compound is prepared in the same way as 2, except that 2-methylimidazole is used in place of imidazole, relying on the observations of B. Tarnchompoo et al., (Tetrahedron Lett. 31:5779–5780, 1990).

Synthesis of 2-(BODIPY® Hydrazido ketoethyl)imidazole (4).

This compound is prepared from BODIPY® Hydrazide and 2 in the same way that BO-IMI is prepared from BODIPY® Hydrazide and N-acetylhistidine.

Synthesis of 2-(BODIPY® Hydrazido ketopropyl)imidazole (5).

This compound is prepared from BODIPY® Hydrazide and 3 in the same way that 4 is prepared.

Synthesis of 2-(Biotin Hydrazido ketoethyl imidazole (6).

This compound is prepared from biotin hydrazide in the same way that 4 is prepared. An analog can also be prepared using botinyl ε-aminocaproyl hydrazide.

Synthesis of 2-(Methylacridimium phenyl ester propionyl ethylenediamine ketoethyl)imidazole (7).

Compound 2 is coupled to ethylenediamine using a water-soluble carbodiimide, and then to methylacridinium phenyl ester propionyl N-hydroxysuccinimide ester (L. J. Kricka, Ibid., p. 277) using a water-soluble carbodiimide.

Synthesis of 2-(Europium chelate)ethylenediamine ketoethyl)imidazole (8).

This compound is prepared in the same way as 7, except that a europium chelate isothiocyanate (L. J. Kricka, Ibid., p. 251) is used in place of the methylacridimium ester.

Synthesis of 2 -($[^{125}I]$-Iodophenethylaminoketopropionyl)imidazole (9).

$[^{125}I]$-Iodophenethylamine is prepared as described (J. E. T. Corrie and W. M. Hunter, Meth. Enzymol. 73:90, 1981) and reacted with 3 in the presence of a water-soluble carbodiimide.

Synthesis of 2-(Digoxigenin-3-O-methylcarbonyl-ε-amino caproyl ethylenediamine ketoethyl)imidazole (10).

This compound is prepared in the same way as 7, except that Digoxigenin-NHS-ester (Boehringer, Mannheim, Germany) is used in place of the methylacridinium ester.

Synthesis of 2-(BODIPY® 581/591 $C_3$-SE ethylenediamine ketoethyl)imidazole (11).

This compound is synthesized in the same way as compound 7, except that BODIPY® 581/591 $C_3$-SE (D-2228, Molecular Probes) is used in place of the methylacridinium ester.

Synthesis of 2-(Pyrenyl-butyryl ethylenediamine ketoethyl)imidazole (12).

This compound is synthesized in the same way as compound 7, except that succinimidyl 1-pyrenebutyrate (S-130, Molecular Probes) is used in place of methylacridinium ester.

Synthesis of 2-(Texas Red sulfonyl ethylenediamine ketoethyl)imidazole (13).

This compound is synthesized in the same way as compound 7, except that Texas Red sulfonyl chloride (T-353) is used in place of the methylacridinium ester.

Use

Numerous applications are possible using the compounds and method of the invention. For example, the method of the invention can be used to measure DNA adducts, or abnormal deoxynucleotides, which are a consequence of covalent damage to DNA by toxic chemical and physical conditions. DNA is an ultimate target in the body for environmental chemicals and conditions that cause cancer and genetic diseases. Thus, the measurement of DNA adducts is of great interest as a means to determine the risk to human health from exposure to toxic chemical and physical conditions. DNA adducts have been measured as damaged mononucleotides by a technique called $^{32}P$ postlabeling thin layer chromatography in which the formed nucleotides are radiolabeled enzymatically with a $^{32}P$ phosphate. Unfortunately, this technique has many disadvantages. Not all DNA adducts are labeled or to the same degree, substances other than nucleotides can be labeled the enzymes are expensive, and, for mononucleotides, one is restricted to labeling those bearing a 3' phosphate. The method of the invention overcomes these problems by providing specific, single step, nonenzymatic labeling which is successful for both 3' and 5' mononucleotides. Further, it is advantageous to label DNA adducts with a fluorescent rather than $^{32}P$ label as in the preferred embodiment of the invention because of the speed, high resolution and high sensitivity provided by capillary electrophoresis with laser fluorescence detection.

Figure 3:
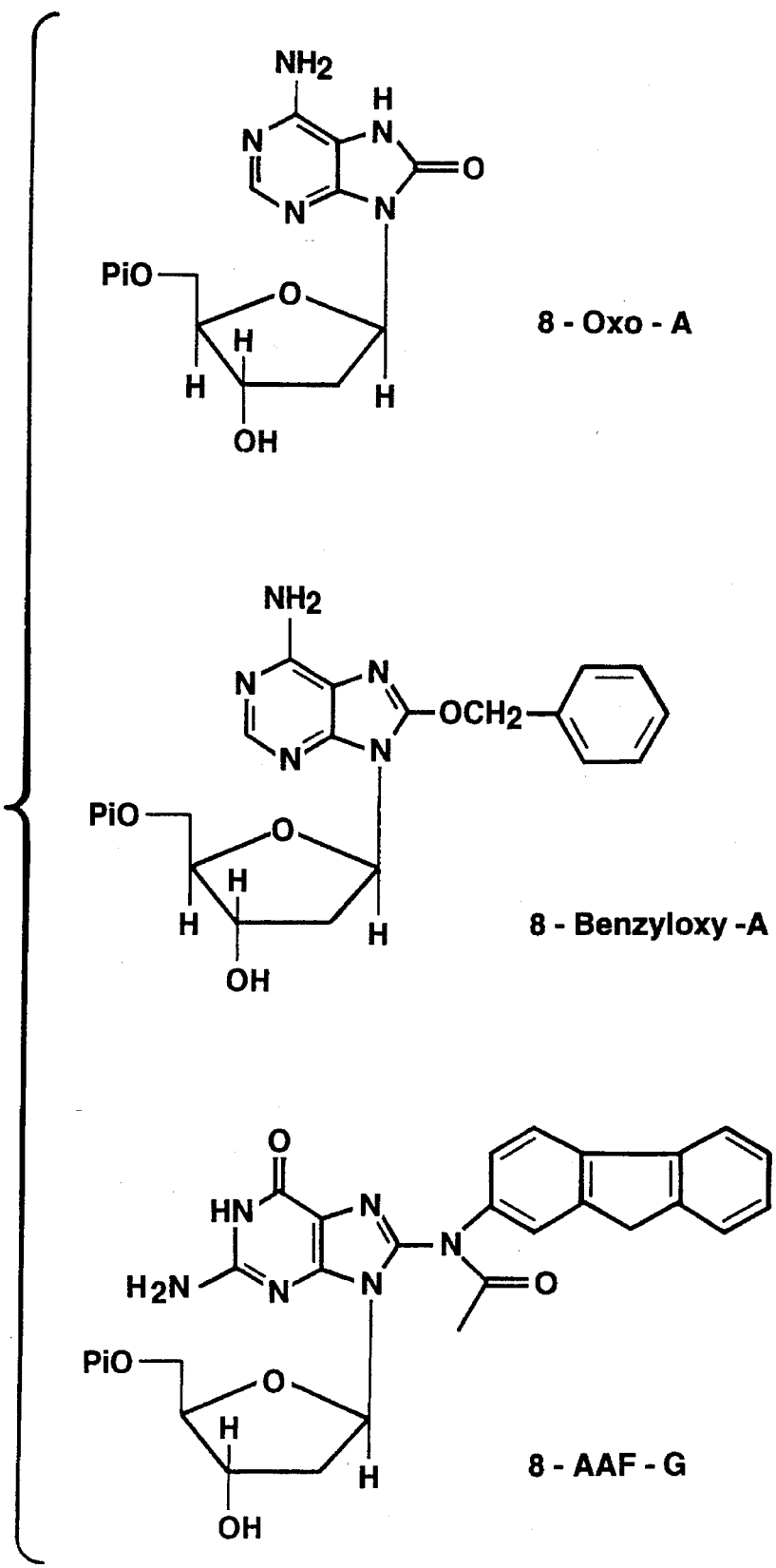
FIG. 3 shows DNA adducts identifiable using the signal group-imidazole labeling compound of the invention.
Figure 4:
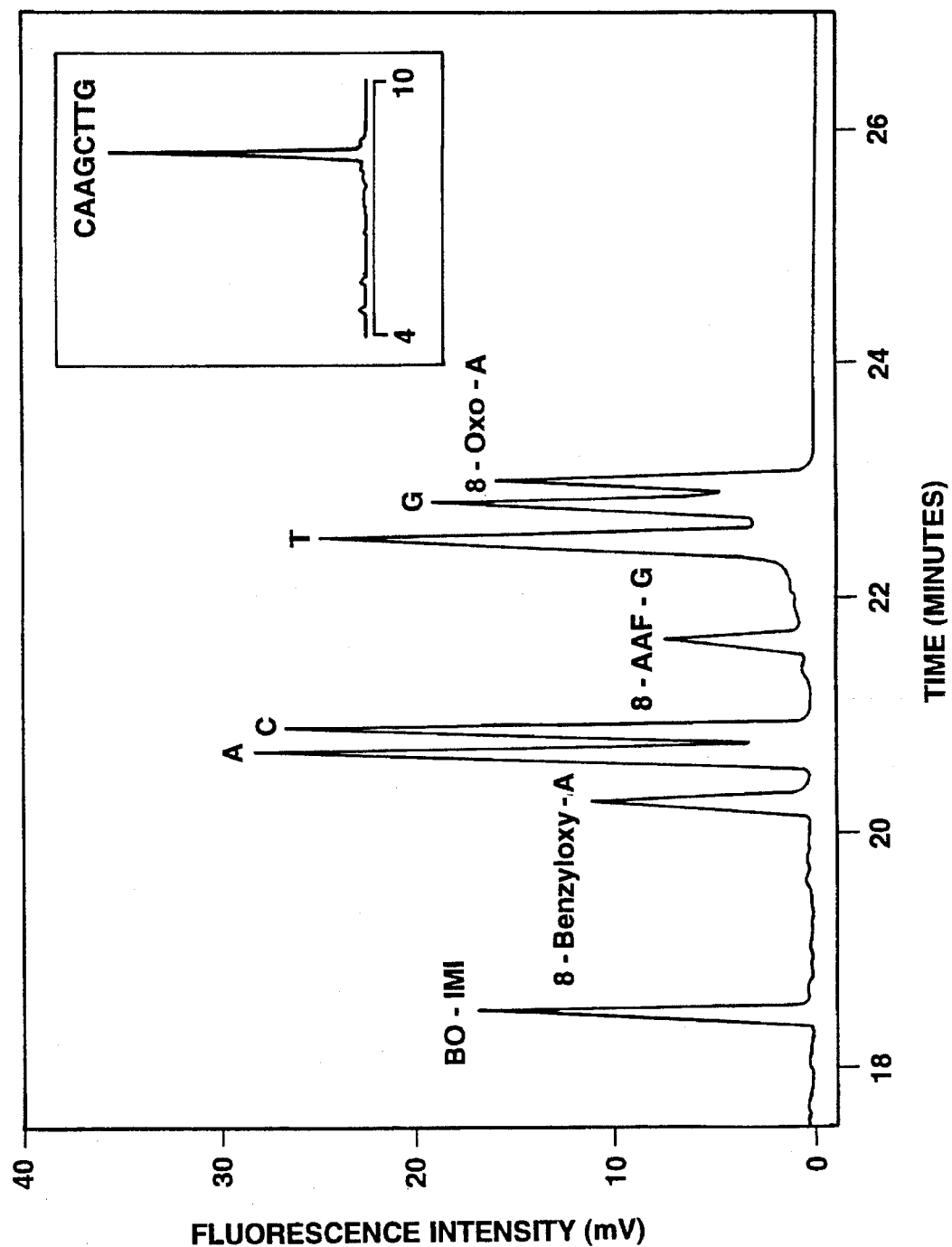
FIG. 4 shows capillary electrophoresis separation of a mixture of nucleotides, including the compounds shown in FIG. 3, labeled with a labeling compound of the invention.

The structures of some commonly produced DNA adducts are shown in FIG. 3. These compounds are 8-oxo-2'-deoxyadenosine-5'-monophosphate (8-Oxo-A), 8-benzyloxy-2'-deoxyadenosine- 5'-monophosphate (8-Benzyloxy-A), and 8-(N-acetyl-2-aminofluorene)-2 '-deoxyguanosine-5'-monophosphate (8-AAF-G). Referring to FIG. 4, an electropherogram from capillary electrophoresis with laser fluorescence detection of a mixture of labeled deoxynucleotide monophosphates from undamaged DNA and labeled DNA adduct is shown. Clear separation and detection of all of the monophosphates in the mixture following labeling with BO-IMI has been obtained. The inset to FIG. 4 shows an electropherogram of a BO-IMI labeled DNA oligomer possessing a 5' phosphate.

DNA probes bearing a terminal phosphate monoester can also be labeled by the method of the invention. Such probes are widely employed in hybridization assays, for example to detect genes, mutations in genes, DNA fingerprints for forensic analysis, and infectious disease agents. The method of the invention will be particularly advantageous for the labeling of probes that may be contaminated with proteins, amino acids or similar substances.

The covalent imidazole labeling technique of the invention opens up a way, for the first time, to achieve staining of biological samples, such as tissue slices, to locate susceptible phosphate compounds. Any of the detectable groups mentioned above will be appropriate for histochemical labeling.

Among the many types of biological molecules, some within each class bear one or more phosphate groups. These phosphate-bearing sub-classes of biomolecules, for example carbohydrate-phosphates, amino acid-phosphates, protein-phosphates, and lipid-phosphates, now can be detected and quantified in a new way since they can be specifically labeled in the method of the invention. The phosphate moiety on these compounds tends to make them water-soluble which is consistent with the conditions of the method of the invention. When multiple phosphate compounds are present in a given sample, the labeling step can be followed by chromatography or electrophoresis, e.g. with fluorene detection, to quantify each of the labeled phosphate substances of interest.

While the technique of the invention achieves relatively stable labeling of some phosphate compounds, it is also an advantage that the labeling can be reversed at a low pH or by the addition of imidazole. This means that a phosphate substance can first be labeled with one label, then this can be reversed and the phosphate substance then can be labeled with a second label. This may be helpful to increase the characterization of a target substance of interest, or to make a given DNA probe more versatile in its applications. It can also allow the substance of interest to be recovered in an intact form for further characterization by other techniques.

The method of the invention, because it achieves relatively specific and stable attachment of the labeled reagent to a phosphate moiety, can also be employed as a general procedure for connecting a substance of interest to a second substance of interest such as an antibody (e.g., to achieve an immunotoxin) or to a chromatographic particle (e.g., to achieve affinity chromatography). Here the low pH or imidazole reversibility can be put to advantage in each of these applications, to later separate the two substances of interest under mild conditions.

Other embodiments will easily be apparent to those of skill in the art and are limited only by the appended claims and equivalents thereof.

What is claimed is:

1. A method for labeling an organic substance containing a free phosphate moiety in aqueous solution comprising the steps of:

providing a signal group-imidazole labeling compound having the structure S—L—I, said labeling compound comprising:

an imidazole moiety (I) wherein I is imidazole or a substituted imidazole wherein one of the three carbon atoms of I is substituted with a $C_1$–$C_6$ alkyl substituent, which in turn is substituted with 0–2 of the following substituents: hydroxy, ether, cyano, amide, ester, vinyl, aryl, sulfate, sulfonate, halogen or sulfonamide; and a signal group S, wherein said signal group S is connected to one of the carbon atoms on the imidazole ring of said imidazole moiety I by a linking group L, and wherein when I is said substituted imidazole, said carbon atom to which L is connected is one of the two non-substituted carbon atoms of I; and wherein further the atoms of L that form a continuous chain between S and I, said atoms of L being denominated the L backbone, number no more than 12;

the L backbone comprises at least one saturated atom when S is a boron-containing fluorescent moiety; and S and L are each devoid of sulfhydryl, primary amino, arylhydroxy and carboxyl group;

adding said compound to a solution containing an organic substance comprising a free phosphate moiety; and covalently linking said labeling compound via the imidazole moiety, in the presence of an aqueous carbodiimide reagent, to free phosphate moiety on said organic substance.

2. The method of claim 1 wherein in said labeling compound in said providing step, L is connected to one of the two adjacent carbon atoms on I.

3. The method of claim 1 wherein in said labeling compound in said providing step, L is connected to carbon 2 (C-2) on I.

4. The method of claim 1 wherein in said labeling compound in said providing step, I is said substituted imidazole.

5. The method of claim 1 wherein in said labeling compound in said providing step, L possesses a branching substituent on the atom that attaches L to I.

6. The method of claim 5 wherein in said labeling compound in said providing step, the atom that attaches L to I is C.

7. The method of claim 1 wherein in said labeling compound in said providing step, L possesses a branching substituent on the penultimate atom that attaches L to I.

8. The method of claim 1 wherein in said labeling compound in said providing step, the number of atoms in the L backbone is 2–8.

9. The method of claim 1 wherein in said labeling compound in said providing step, said linking group L further includes 0–1 amino acid residues.

10. The method of claim 1 wherein in said labeling compound in said providing step, said linking group L further includes 0–1 amino acid residues.

11. The method of claim 1 wherein in said labeling compound in said providing step, S is a fluorophore.

12. The method of claim 11 wherein in said labeling compound in said providing Step, S is a fluorophore with an absorption maximum $\geq 450$ nm.

13. The method of claim 11 wherein in said labeling compound in said providing step, S is a boron-containing fluorophore.

14. The method of claim 1 wherein in said labeling compound in said providing step, S is a lanthanide chelate.

15. The method of claim 1 wherein in said labeling compound in said providing step, S is a lumiphore.

16. The method of claim 1 wherein in said labeling compound in said providing step, S is luciferin, a dioxetane, or an acridinium ester.

17. The method of claim 1 wherein in said labeling compound in said providing Step, S is radioactive.

18. The method of claim 17 wherein in said labeling compound in said providing step, S contains $^{32}P$, $^{33}P$, $^{125}I$, $^{35}S$, $^{3}H$ or $^{14}C$.

19. The method of claim 1 wherein in said labeling compound in said providing step, S is an azo dye.

20. The method of claim 1 wherein in said labeling compound in said providing step, S is a hapten.

21. The method of claim 1 wherein in said labeling compound in said providing step, S is digoxigenin or an aryl hapten.

22. The method of claim 1 wherein in said labeling compound in said providing step, S is an electrochemiphore.

23. The method of claim 1 wherein in said labeling compound in said providing step, S is a sugar.

24. The method of claim 1 wherein in said labeling compound in said providing step, S is an organometallic or metal chelate.

25. The method of claim 1 wherein in said labeling compound in said providing step, S is an oligonucleotide.

26. The method of claim 1 wherein in said labeling compound in said providing step, S is an electrophore.

27. The method of claim 1 wherein in said labeling compound in said providing step, S is a fluorine-containing electrophore.

28. A signal group-imidazole labeling compound of the formula

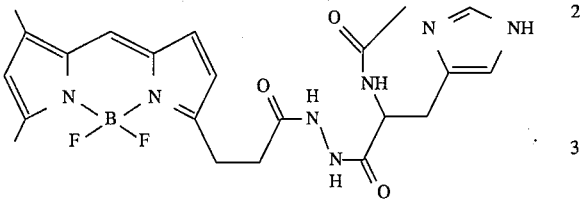

29. A molecular conjugate comprising a signal group-imidazole labeling compound having the structure S—L—I, said labeling compound comprising:

an imidazole moiety (I) wherein I is imidazole or a substituted imidazole wherein one of the three carbon atoms of I is substituted with a $C_1$–$C_6$ alkyl substituent, which in turn is substituted with 0–2 of the following substituents: hydroxy, ether, cyano, amide, ester, vinyl, aryl, sulfate, sulfonate, halogen or sulfonamide; and a signal group S, wherein said signal group S is connected to one of the carbon atoms on the imidazole ring of said imidazole moiety I by a linking group L, and wherein when I is said substituted imidazole, said carbon atom to which L is connected is one of the two non-substituted carbon atoms of I; and wherein further the atoms of L that form a continuous chain between S and I, said atoms of L being denominated the L backbone, number no more than 12;

the L backbone comprises at least one saturated atom when S is a boron-containing fluorescent moiety; and S and L are each devoid of sulfhydryl, primary amino, arylhydroxy and carboxyl groups, said labeling compound being covalently bound via said imidazole moiety to a free phosphate moiety on an organic biomolecule.

30. A method for labeling an organic substance containing a free phosphate moiety in aqueous solution comprising the steps of:

providing a signal group-imidazole labeling compound of the formula:

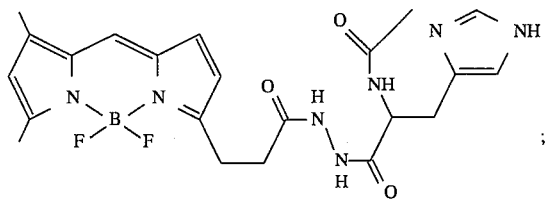

adding said compound to a solution containing an organic substance comprising a free phosphate moiety; and covalently linking said labeling compound via the imidazole moiety, in the presence of an aqueous carbodiimide reagent, to a free phosphate moiety on said organic substance.

31. A molecular conjugate comprising the signal group-imidazole labeling compound of the formula:

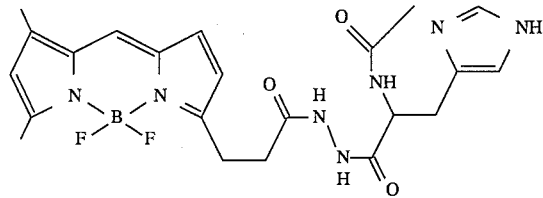

covalently bound via the imidazole moiety to a free phosphate moiety on an organic biomolecule.

* * * * *